(12) United States Patent
Haueter et al.

(10) Patent No.: US 8,277,434 B2
(45) Date of Patent: Oct. 2, 2012

(54) DOSING DEVICE FOR AN INFUSION SYSTEM AND METHOD THEREOF

(75) Inventors: Ulrich Haueter, Grosshochstetten (CH); Florian Kuehni, Wabern (CH)

(73) Assignee: Roche Diagnostics International AG, Rotkreuz (CH)

( * ) Notice: Subject to any disclaimer, the term of this patent is extended or adjusted under 35 U.S.C. 154(b) by 0 days.

(21) Appl. No.: 13/097,894

(22) Filed: Apr. 29, 2011

(65) Prior Publication Data

US 2011/0208154 A1 Aug. 25, 2011

Related U.S. Application Data

(60) Division of application No. 12/559,851, filed on Sep. 15, 2009, now Pat. No. 7,955,302, which is a continuation of application No. PCT/EP2008/001516, filed on Feb. 26, 2008.

(30) Foreign Application Priority Data

Mar. 15, 2007 (EP) .................................. 07104240

(51) Int. Cl.
*A61M 31/00* (2006.01)
(52) U.S. Cl. ........................................................ 604/500
(58) Field of Classification Search ............... 604/65, 604/67, 131, 151, 246, 247, 248
See application file for complete search history.

(56) References Cited

U.S. PATENT DOCUMENTS

| | | | |
|---|---|---|---|
| 3,631,654 A | | 1/1972 | Riely et al. |
| 4,643,723 A | * | 2/1987 | Smit ............................. 604/207 |
| 5,014,750 A | * | 5/1991 | Winchell et al. ................ 138/43 |
| 5,033,714 A | * | 7/1991 | Winchell et al. ............... 251/127 |
| 5,045,096 A | | 9/1991 | Quang et al. |
| 5,100,389 A | * | 3/1992 | Vaillancourt .................. 604/135 |
| 5,207,666 A | * | 5/1993 | Idriss et al. ................. 604/891.1 |
| 5,547,110 A | * | 8/1996 | Keller et al. ................... 222/219 |
| 5,807,321 A | | 9/1998 | Stoker et al. |
| 6,010,485 A | * | 1/2000 | Buch-Rasmussen et al. 604/191 |
| 6,179,583 B1 | * | 1/2001 | Weston ........................ 417/392 |
| 6,749,587 B2 | * | 6/2004 | Flaherty ....................... 604/151 |
| 7,887,308 B2 | * | 2/2011 | Navarro ....................... 417/461 |

(Continued)

FOREIGN PATENT DOCUMENTS

DE 3832028 A1 3/1990

(Continued)

OTHER PUBLICATIONS

International Search Report, PCT/EP2008/001516, Mar. 4, 2008.

(Continued)

*Primary Examiner* — Nicholas Lucchesi
*Assistant Examiner* — Aarti B Berdichevsky
(74) *Attorney, Agent, or Firm* — Dinsmore & Shohl LLP

(57) ABSTRACT

A dosing device for an infusion system comprises a dosing unit having a variable volume and at least one opening in fluid connection with the variable volume, through which opening the variable volume can be filled with a substance or the substance can be dispensed from the variable volume. The dosing device is operable in a first state for filling the substance from a supply conduit, in a second state for preventing filling and dispensing, or in a third state for dispensing through a dispensing conduit. No direct fluid connection exists between the supply conduit and the dispensing conduit at any time. Methods for dosing a substance with the dosing device.

4 Claims, 3 Drawing Sheets

U.S. PATENT DOCUMENTS

| | | |
|---|---|---|
| 2001/0025189 A1 | 9/2001 | Haueter et al. |
| 2004/0069044 A1* | 4/2004 | Lavi et al. .................. 73/1.73 |
| 2005/0033148 A1 | 2/2005 | Haueter et al. |
| 2005/0159708 A1* | 7/2005 | Sidler ..................... 604/132 |
| 2009/0196775 A1* | 8/2009 | Navarro ................... 417/460 |
| 2010/0049127 A1 | 2/2010 | Haueter et al. |

FOREIGN PATENT DOCUMENTS

| | | |
|---|---|---|
| EP | 0 980 690 A2 | 2/2000 |
| EP | 1 486 218 A2 | 12/2004 |
| EP | 1 754 505 A1 | 2/2007 |
| EP | 1970677 A1 | 9/2008 |
| WO | 2006056828 A1 | 6/2006 |
| WO | 2007/000064 A1 | 1/2007 |
| WO | 2007141681 A2 | 12/2007 |
| WO | 2008/110263 A1 | 9/2008 |

OTHER PUBLICATIONS

Notice of Allowance pertaining to U.S. Appl. No. 13/097,880, dated Apr. 2, 2012.

* cited by examiner

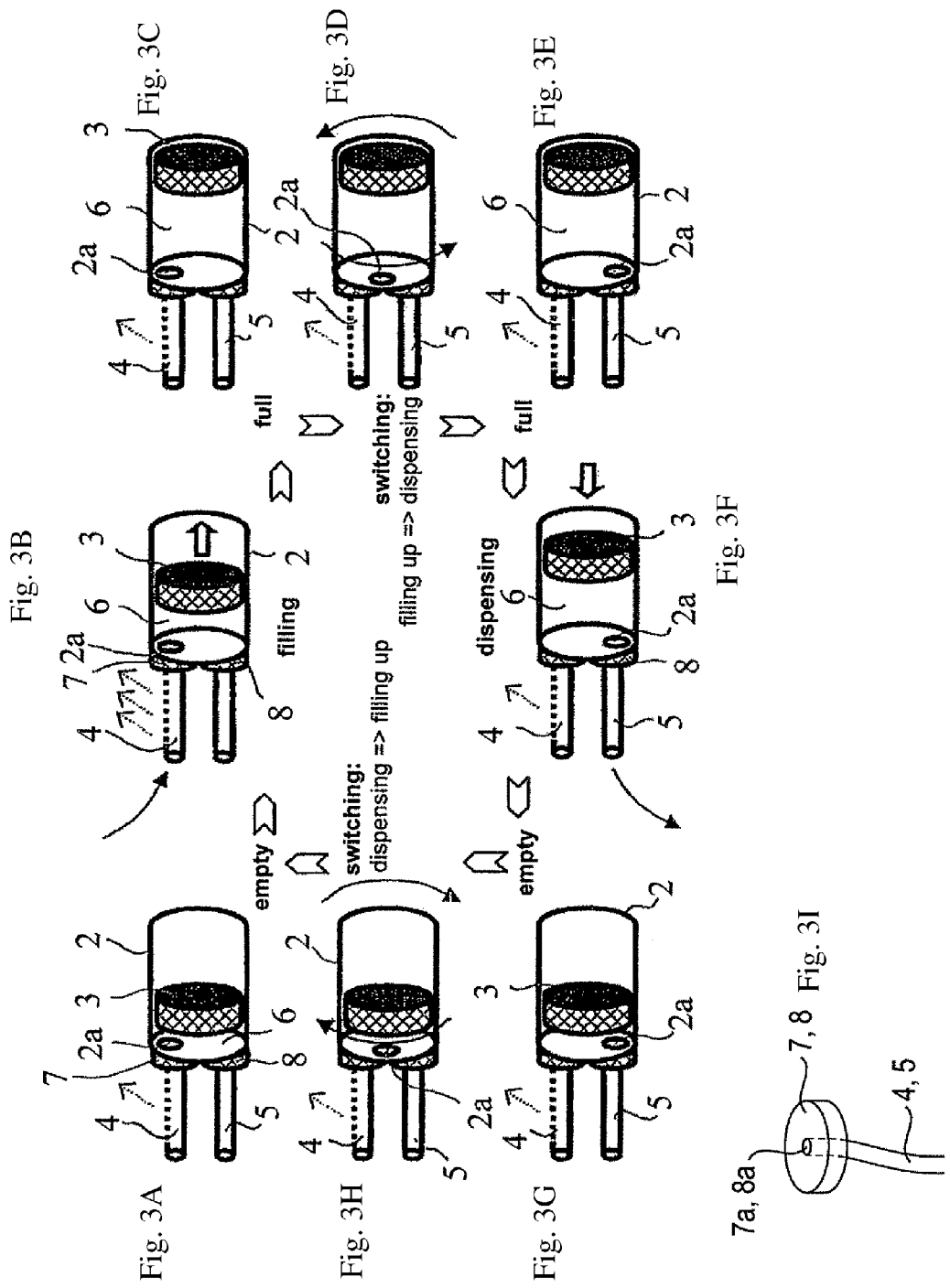

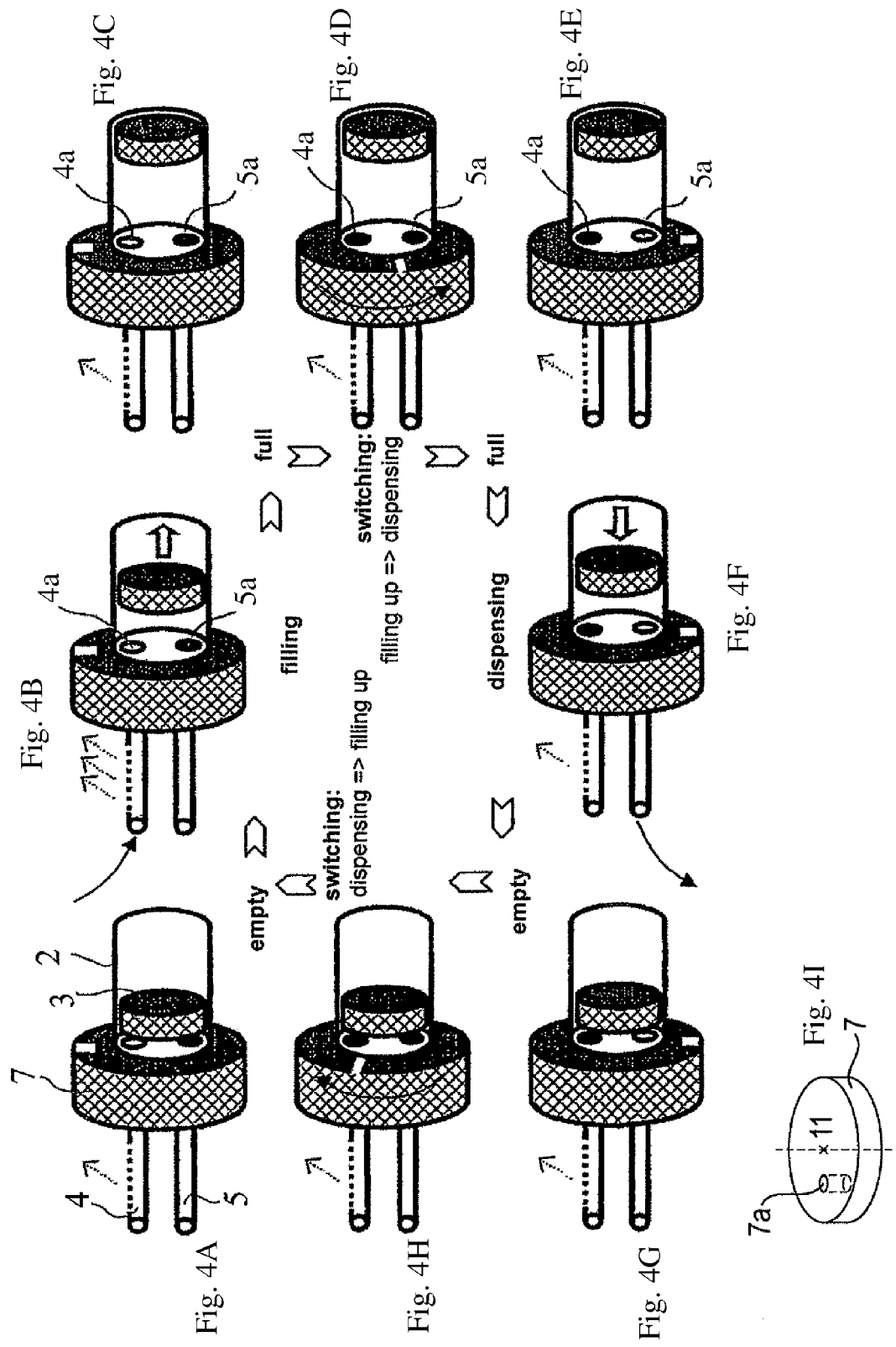

DOSING DEVICE FOR AN INFUSION SYSTEM AND METHOD THEREOF

CROSS-REFERENCE TO RELATED APPLICATIONS

The present application is filed under 35 U.S.C. §111(a) as a divisional of U.S. application Ser. No. 12/559,851 filed Sep. 15, 2009, now U.S. Pat. No. 7,955,302 which is a continuation of International Application No. PCT/EP2008/001516, with an international filing date of Feb. 26, 2008, which claims priority under 35 U.S.C. §119 to European Patent Application No. 07104240.2, filed Mar. 15, 2007.

TECHNICAL FIELD

The described embodiments relate to a dosing and conveying device and in particular to a device for dosing a substance to be dispensed.

BACKGROUND

CH 688 224 A5 discloses an implantable device for dispensing pharmaceutical fluids in the human or animal body in doses, wherein the implantable unit comprises: a cam-controlled, valve-less axial piston pump comprising a piston which can be rotary-driven and axially displaced; a fluid reservoir which is connected to the suction side of the pump; and a rotary drive which is connected to the piston and can be controlled, wherein a suction opening and a pressure opening are each arranged on a lower end of a cylinder, and the two openings lie diametrically opposite each other and run in the same axis.

U.S. Pat. No. 6,010,485 discloses a working cylinder having a similar design to that in CH 688 224 A5.

U.S. Pat. No. 6,749,587 B2 discloses a modular infusion apparatus comprising a measuring portion which can directly control the fluid flow between a reservoir and a cannula. If the reservoir is kept at ambient pressure, the measuring portion can comprise a peristaltic mechanism, a displacement pump or other pump device.

U.S. Pat. No. 4,643,723 discloses a device for administering insulin to a patient, wherein a piston is arranged in a pump chamber, a cannula is connected to the pump chamber, and a piston rod is connected to the piston. When the piston is retracted, the reservoir is connected to the pump chamber in order to fill up the pump chamber, and when the piston is moved forwards, the passage from the reservoir to the pump chamber is closed by means of a valve, such that the substance can be administered via a cannula.

WO 93/04714 and the corresponding EP 0 600 948 B1 disclose a fluid measuring element for an implantable administering system which is coupled between a pressurized fluid source and an outlet opening, in order to provide discrete flow pulses at a predetermined rate.

US 2004/0069044 A1 discloses a device for measuring a volume of a drug. The device comprises a first chamber which contains the fluid drug, a measuring chamber which is in fluid connection with the first chamber, and a measuring array.

U.S. Pat. No. 5,207,666 discloses a fluid measuring apparatus for implantable drug administering systems, which can be arranged between a pressurized fluid source and an outlet opening, in order to provide discrete flow pulses at a predetermined rate.

US 2005/0159708 A1 discloses an infusion pump for administering a fluid in doses, wherein a piston is permanently pressurized by means of a spring and acts on a drug container which dispenses the substance through a dispensing opening towards a control valve, in order to dose it.

EP 1 633 417 B1 discloses a dispensing apparatus comprising a storage chamber and an injection chamber which are coupled via a fluid connection and in each of which plungers are arranged.

There remains a need for a dosing device for an infusion system that enables a substance to be dosed precisely and dispensed simply.

SUMMARY

Embodiments of a dosing device for an infusion system comprise a dosing unit having a variable volume. The variable volume may comprise, for example, a cylinder comprising a piston that moves in the cylinder to cause an increase or decrease of the volume of the cylinder. The dosing device comprises at least one supplying/dispensing port. In some embodiments, the supplying/dispensing port may be a single port, such as a single opening, and the single opening may be disposed, for example, on the cylinder, on a part of the port, or on a sleeve. In some embodiments, the single port may remain closed except during supply and dispensing operations. Through the supplying/dispensing opening, the variable volume of the dosing unit can be filled with the substance to be dispensed. The substance may be dispensed, for example, from a storage container such as for example an ampoule, when the volume of the dosing unit is increased. When the variable volume of the filled dosing unit is decreased again, the substance which is to be dispensed in doses can be outputted again through the dispensing opening. The dosing device is preferably designed such that the supplying/dispensing port can be alternately connected to a storage container, such as for example an ampoule, and to a dispensing or administering unit such as, for example, an infusion set.

In an embodiment of a method for dosing a substance to be dispensed from a storage container or a reservoir, the substance is moved from the storage container or reservoir via or through a single port or opening into a dosing unit having a variable volume. The variable volume enlarges during dosing, for example, and decreases in volume during dispensing, for example. Once the variable volume has been filled, the port or opening is connected to a dispensing conduit and the variable volume containing the substance is then decreased in volume to dispense the substance in doses through the port or opening. In some embodiments, after the variable volume has been filled with the substance to be dispensed, the dosing unit may be displaced or rotated to decouple the opening of the dosing unit from the supply conduit and to connect the dosing unit to the dispensing conduit.

BRIEF DESCRIPTION OF THE DRAWINGS

The invention is described below on the basis of example embodiments, wherein:

FIGS. 3A-3I show an embodiment of a cyclic process for using the dosing device; and FIGS. 4A-4I show a further embodiment of a cyclic process for using the dosing device.

DETAILED DESCRIPTION

Figures 1A, 1B, 1C:
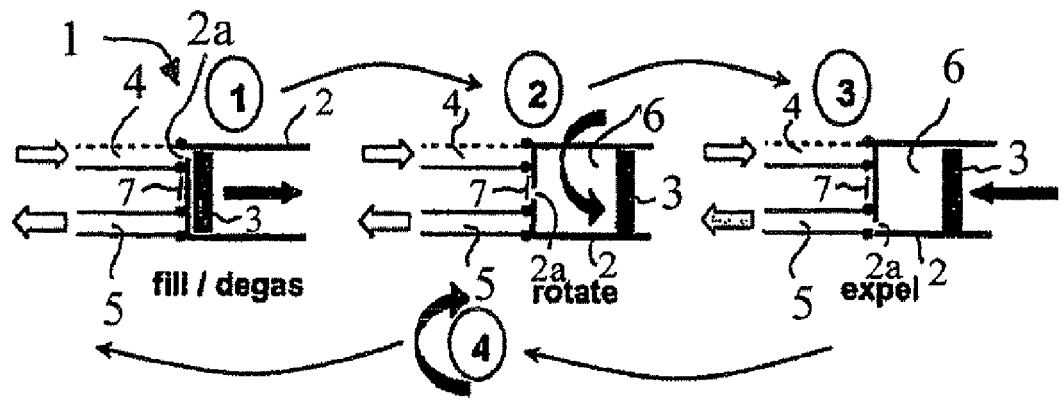
FIGS. 1A, 1B, 1C illustrate an example operational sequence for dosing using the dosing device.

Embodiments of a dosing device for an infusion system comprise a dosing unit comprising a variable volume. The variable volume may comprise, for example, a cylinder comprising a piston that moves in the cylinder, thereby increasing or decreasing the volume of the cylinder. The dosing device comprises a supplying/dispensing port. In some embodiments, the supplying/dispensing port may be a single port, such as a single opening. The single opening may be disposed, for example, on the cylinder, on a part of the port, or on a sleeve. In some embodiments, the single port may remain closed except during supply and dispensing operations. Through the supplying/dispensing opening, the variable volume of the dosing unit can be filled with the substance to be dispensed. The substance may be dispensed, for example, from a storage container such as for example an ampoule, when the volume of the dosing unit is increased. When the variable volume of the filled dosing unit is decreased again, the substance which is to be dispensed in doses can be outputted again through the dispensing opening. The dosing device is preferably designed such that the supplying/dispensing port can be alternately connected to a storage container, such as for example an ampoule, and to a dispensing or administering unit such as, for example, an infusion set.

It is thus possible to prevent leakage and the unintentional or uncontrolled passage of a substance from a reservoir to a dispensing unit such as an infusion set, because the dosing unit is coupled either to the reservoir only or to the administering device only. The reservoir is thus completely decoupled from the administering unit, such that the reservoir is never directly connected to the outlet. The substance can be dispensed so as to be precisely dosed by a dosing device, independently of the design and size of a reservoir or storage container. Also, if a single supplying/dispensing opening is used, the dosing unit exhibits a relatively small leakage or sealing risk.

In some embodiments, the supplying/dispensing port may comprise a plurality of openings that may be connected to an external port always and in such a way that the dosing unit is either only being filled or only being emptied through all or some of the openings. By such a configuration it is not possible to simultaneously receive and dispense a substance. The connection or access or hole of the dosing unit that acts as inlet or outlet, alternatively the plurality of connections or accesses or holes of the dosing unit that simultaneously act as an inlet or outlet, can be coupled such that they can either be coupled to a reservoir (and act as an inlet for the dosing unit) or can be coupled to an administering device, such as for example an infusion apparatus, and so act as an outlet for the dosing unit. In example embodiments, the ports of the dosing unit may be sealed when a substance is not being received or dispensed.

In some embodiments the openings may be actively sealed in a resting position between dispensing and receiving a substance. The active sealing may be accomplished, for example, by a sealing element that can be displaced.

In some embodiments the dosing unit may be displaced or rotated to be connected to one of two or more external ports to fill the dosing unit or to dispense and relay the substance dispensed from the dosing unit, depending on the displaced position or rotational position. One or more of the external ports also may be disposed on the dosing unit in such a way that the external ports can be displaced or rotated. In example embodiments, the ports that can be displaced may be alternately connected to the supplying/dispensing opening of the dosing unit, for example. A valve effect can thus be obtained by a kind of switching valve.

Some embodiments of the dosing device may comprise a motor configured to move, or for example, to rotate or displace the dosing unit or the supplying/dispensing port of the dosing unit. The motor can alternatively or additionally be used to move (for example, to displace or rotate) the external supplying/dispensing ports so as to alternately connect the supplying/dispensing ports to the supplying/dispensing opening of the dosing unit. The motor or an additional motor can be used to move the piston to shrink or enlarge the variable the volume. The piston of the cylinder is preferably designed to be moveable precisely to a predetermined position within the cylinder. For example, the piston may be moveable exactly to a predefined maximum drawn-out position of the piston still situated within the cylinder. Thereby, unlike in known, so-called "single-stroke" methods, in the present embodiments it is possible to use only some of the variable volume for dosing.

In some embodiments the connecting points or connecting conduits that lead to the supplying/dispensing port of the dosing unit comprise at least one valve each. Alternatively, only a single valve may be provided, for example, in the supply conduit, in the dispensing conduit, or in the supplying/dispensing port. Such a valve in one or both of the conduits, for example as a reflux valve, can ensure that a substance to be dispensed in doses is conveyed in only one direction. Thereby, backflow of the substance in the opposite direction is inhibited or prevented.

In example embodiments, the valve or valves used on or in the supply conduits, the drainage conduits, the dosing unit, or any combination thereof, can be reflux valves that enable the flow of a substance or fluid in only one direction. Alternatively, the valves can be designed as pressure-relief valves that enable the passage of a material or fluid only when a minimum pressure is applied.

The storage container that contains the substance to be dispensed can be pressurized or non-pressurized. In example embodiments, the storage container may be an ampoule, for example. The ampoule may comprise a pressurized stopper that acts on the substance to be dispensed, such that the substance to be dispensed may be dosed without requiring additional energy to dispense the substance from the ampoule, to dose the dosing unit, to refill the dosing unit, or any of these. In some embodiments, the stopper may be pressurized by means such as, for example, a spring or a pressurized gas. Alternatively, the storage container may comprise an elastic region or may be formed entirely of an elastic material. In example embodiments, the storage container may be configured as a pouch filled with the substance to be dispensed. To displace and dispense the substance contained in the storage container, in example embodiments a force or pressure can act on the elastic region or pouch by means of a spring. The spring may be enabled by the dosing device downstream of the storage container.

In some embodiments, the storage container or reservoir may be configured such that a positive pressure may be applied at an outlet or dispensing opening of the reservoir. In example embodiments, the positive pressure at an outlet or opening may be achieved by containers or pouches that are pressurized or charged with a force. Alternatively, the positive pressure may be achieved by an active drive mechanism that acts on a displacement element of the reservoir or on the reservoir itself.

In some embodiments, the dosing device may comprise at least one sensor for checking the functional capability or determining a malfunction. Examples of such sensors include, but are not limited to, a leakage sensor, a galvanic or conductance sensor, a bubble sensor, a pressure sensor, or a force sensor. Such sensors are operative to determine, for example, whether a substance or fluid has escaped from the dosing device, whether the substance to be dispensed contains bubbles, or whether an occlusion is present. In further embodiments, said at least one sensor may be connected to a warning or alarm indicator or to a controller of the dosing device. The indicator or controller may be configured to switch off the dosing device when a malfunction is determined. Alternatively, the indicator or controlled may be configured to output an alarm signal when a fault in the dosing device is determined. Example alarm signals include, for example, an optical or acoustic alarm signal.

In some embodiments, the dosing device, the connecting conduits (for example, the supply conduit or the dispensing conduit), or both, may comprise a material that is permeable to gas or air. If air or a gas is present in the substance to be dispensed, then a gas-permeable or air-permeable supplying tube that connects the dosing device to the storage container upstream of dosing can enable the gas in the substance to escape when the substance is guided through said conduit. Thereby, no gas pockets will be present in the substance in the dosing unit.

In some embodiments, a seal such as, for example, a sealing collar, may be disposed on the dosing device to seal off the supplying/dispensing port of the dosing unit when the port is not connected to a supply conduit or a dispensing conduit. The port is not connected to a conduit, for example, when the port is rotated together with the dosing unit from the connection to the supply conduit to the connection to the dispensing conduit.

FIGS. 1A-1C show a non-limiting, example embodiment of a dosing device 1. The dosing device 1 comprises a dosing unit 2, shown in the example embodiment to be configured as a cylinder, comprising a supplying/dispensing port (configured as a single opening 2a) disposed on one side of the dosing unit 2. In an initial configuration shown in FIG. 1A, before the dosing unit 2 is filled, the single opening 2a is connected to a supply conduit 4, which is connected to a reservoir (not shown), for example a pressurized reservoir, which contains a substance to be dispensed in doses, such as for example insulin. In the example embodiment, a movable piston 3 is arranged in the dosing unit 2.

FIG. 1B shows the state of the embodiment of the dosing device 1 from FIG. 1A, after the dosing unit 2 has been dosed. The dosing unit 2 may be dosed, for example, by retracting the piston 3 within the dosing unit 2 to introduce a substance through the supply conduit 4, into the variable volume 6 of the dosing unit 2. Once the filling process has been completed, the dosing unit 2 in FIG. 1B has already been rotated slightly about its longitudinal axis, as indicated by the arrow, such that the single opening 2a of the dosing unit 2 is no longer connected to the supply conduit 4 or is no longer in fluid communication with the supply conduit 4. In the state shown in FIG. 1B, the single opening 2a has been displaced or rotated toward a dispensing conduit 5, and the single opening 2a is sealed by means of a seal 7 that abuts the dosing unit 2.

If the dosing unit 2 is rotated until the single opening 2a abuts the dispensing conduit 5, as shown in FIG. 1C, the substance contained in the variable volume 6 can be dispensed to the dispensing conduit 5 through the single opening 2a by sliding the piston 3 into the dosing unit 2. The dispensing conduit 5 may be connected to an infusion set (not shown) or needle (not shown). In example embodiments, after the substance contained in the variable volume 6 of the dosing unit 2 has been partially or completely dispensed, the dosing unit 2 may be rotated with the piston 3 completely slid into the dosing unit 2. After such a rotation, the single opening 2a again abuts the supply conduit 4, as indicated in FIG. 1A by the state (4), so that the cycle shown in FIG. 1 may be repeated.

Figure 2:
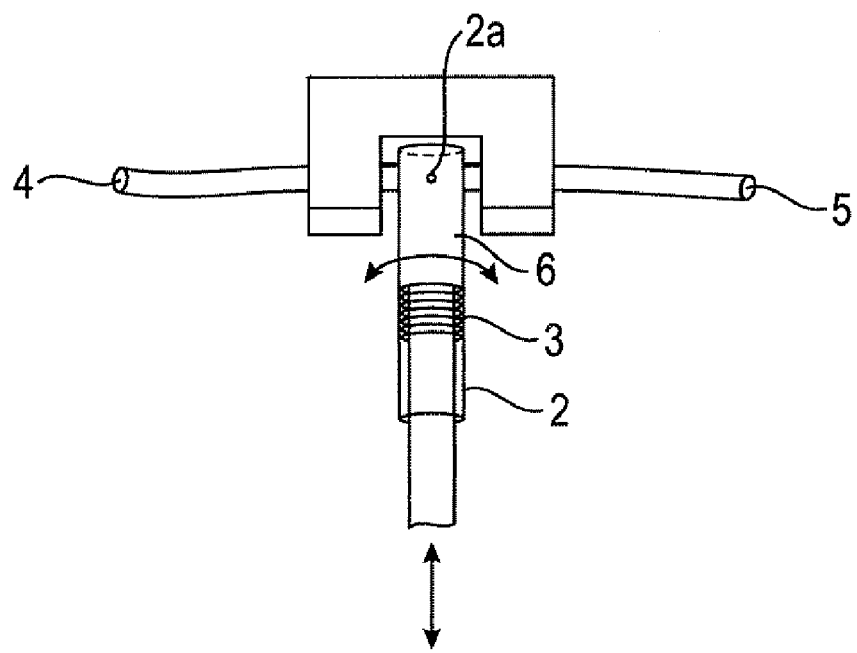
FIG. 2 shows one embodiment of the dosing device.

FIG. 2 shows an example embodiment of a dosing device 1, wherein the dosing device 1 comprises a dosing unit 2. As shown in the example embodiment, the dosing unit 2 may be rotatable. The dosing unit 2 may comprise, for example, a plastic or an elastic material. The dosing unit 2 is disposed between supply conduit 4 and dispensing conduit 5. Supply conduit 4 and dispensing conduit 5 may comprise, for example, an elastic material. Additionally, the dosing unit 2 may be disposed within a sealing sleeve (not shown), for example, and the sealing sleeve may comprise, for example, two openings. When the single opening 2a, which may be disposed on a lateral surface or on the cylinder casing, is connected to the supply conduit 4, the variable volume 6 within the dosing unit 2 can be loaded with a substance by retracting the piston 3 to draw the substance through the supply conduit 4. In some embodiments, the single opening 2a can be a simple hole in the dosing unit 2 that is sealed by the elastic property of the material (such as plastic, for example) of the dosing unit 2. In such a case, the substance can pass through the single opening 2a only when a pressure or suction acts on the substance, such as for example when the piston 3 is drawn out of the dosing unit 2 or when the piston 3 is slid into the dosing unit 2.

In some embodiments, the dosing variable volume of the dosing unit may be incrementally varied, for example in steps or increments. In example embodiments, wherein the dosing unit comprises a single supplying/dispensing port, the single supplying/dispensing port may be disposed asymmetrically. In example embodiments, wherein two or more supplying/dispensing ports are present that can be alternately closed or opened, for example, the supplying/dispensing ports also can be arranged asymmetrically. Each supplying/dispensing port also can be disposed as a simple opening in the dosing unit, such as for example a cylinder. As used herein, the terms "asymmetrical port" and "asymmetrical opening" refer to an opening in the dosing unit or, for example, a cylinder, either of which changes its position about an axis of symmetry when the dosing unit is moved, displaced, or rotated. In example embodiments, an asymmetrical opening can be disposed on the end-facing side of a cylinder, for example, provided it does not lie in the center of the end-facing side but, rather, is offset from the center of the end-facing side. In further example embodiments, the asymmetrical opening can be disposed laterally on the dosing unit or in the cylinder casing.

Once the dosing unit 2 has been dosed through the passage of the substance through the single opening 2a into the dosing unit 2 via the supply conduit 4, the dosing unit 2 is rotated such that the single opening 2a of the dosing unit 2 is connected to the dispensing conduit 5. In the example embodiment, the dosing unit 2 is rotated by 180° about its longitudinal axis. In this state, the piston 3 can be slid back into the dosing unit 2, so as to displace the substance contained in the dosing unit 2. The substance so displaced is dispensed through the open (and self-closing) single opening 2a of the dosing unit 2 to the dispensing conduit 5, which is connected to an infusion set (not shown). The dosing unit 2 then can be rotated back or rotated further until the single opening 2a of the dosing unit 2 is returned to fluid connection with the supply conduit 4 and is thereby readied to receive another dose of the substance through the supply conduit 4.

FIGS. 3A-3H show an example of a cyclic operational sequence for dosing a substance by means of an embodiment of the dosing device 1. In general, the dosing device 1 is operable in one of three states. FIGS. 3A, 3B, and 3C illustrate a first state, in which a substance may be supplied from, for example, a supply conduit 4 to the variable volume 6 through a single opening 2a. FIGS. 3D and 3H illustrate a second state, in which passage of the substance through the single opening 2a is prevented. FIGS. 3E, 3F, and 3G illustrate a third state, in which the substance may be dispensed from the variable volume 6 through the single opening, for example, to a dispensing conduit 5 connected to a dispensing unit (not shown) of an infusion system (not shown). The dosing unit may be rotated, displaced, or both, to select the first state, the second state, or the third state at any given time. Starting from an initial position in FIG. 3A, the dosing unit 2 is empty and the piston 3 is completely or almost completely retracted into the dosing unit 2 toward a supplying/dispensing port (configured as a single opening 2a) on the end-facing side of the dosing unit 2. The dosing unit 2 is filled gradually through the supply conduit 4, which is designed to be permeable to air. As shown in FIG. 3B, the piston 3 is moved within the dosing unit 2 in the direction shown by the arrow, thereby enlarging the variable volume 6. The enlargement of the variable volume 6 results in a negative pressure in the dosing unit 2. The negative pressure causes the substance to be supplied from a reservoir (not shown) and be drawn through the supply conduit 4 or introduced into the dosing unit 2. The dosing unit 2 or the single opening 2a is positioned or rotated to lie as close as possible to the front of the opening of the supply conduit 4, such that a fluid connection is created from the supply conduit 4 to the variable volume 6 through the single opening 2a.

In the embodiment shown, sealing elements 7, 8 may be disposed between the supply conduit 4 and dispensing conduit 5 and the dosing unit 2 on the front side, the connecting side, the contact side, or any combination of these. The sealing elements 7, 8 may be arranged around the openings of the supply conduit 4 and the dispensing conduit 5 to prevent escape of the substance or fluid flowing in the supply conduit 4 or in the dispensing conduit 5. In some embodiments, the sealing elements 7, 8 may comprise, for example, disc-shaped or annular elements, as shown in FIG. 3I, and the elements may comprise, for example, an elastic material. In examples of such embodiments, the dosing unit 2 or an end-facing side of the dosing unit 2 is able to slide easily over the sealing elements 7, 8.

As can be seen from FIG. 3C, the dosing unit 2 is completely filled when the piston 3 has been drawn out up to a maximum position. In the shown example embodiment, wherein the dosing unit is configured as a cylinder comprising a piston, this maximum volume of the variable volume 6 of the dosing unit is referred to as $V_{cylinder,\,max}$. When the dosing unit is configured as a cylinder comprising a piston, the maximum volume of the variable volume ($V_{cylinder,\,max}$) may be defined as the volume of the cylinder when the piston is drawn out as far as desirable for the particular dosing application, for example, completely drawn out or almost completely drawn out. In some embodiments, the dosing device may be configured such that $V_{cylinder,\,max}$ is smaller than 0.1 times the volume of the storage container or a reservoir ($V_{reservoir}$) in which the substance to be dispensed is contained. In some embodiments, the maximum volume $V_{cylinder,\,max}$ may be substantially larger than the volume of a minimum dose to be dispensed ($V_{dose,\,min}$). For example, $V_{cylinder,\,max}$ may be twice $V_{dose,\,min}$ or even, for example, ten times $V_{dose,\,min}$. In some embodiments, the maximum volume of the dosing unit $V_{cylinder,\,max}$ may be equal to the minimum volume of the dose to be dispensed $V_{dose,\,min}$ multiplied by the square root of the ratio of the volume of the reservoir $V_{reservoir}$ to the minimum volume of the minimum dose to be dispensed $V_{dose,\,min}$, according to the following equation:

$$V_{cylinder,max} = V_{dose,min} \times \sqrt{(V_{reservoir}/V_{dose,min})}.$$

Thus, in some embodiments the dosing device may be configured such that:

$$x \times V_{dose,\,min} < V_{cylinder,\,max} < y \times V_{reservoir}, \text{ where } 2 < x < 10 \text{ and } 0.1 < y < 0.5.$$

In some embodiments, the ratio of the inner diameter of a cylindrical dosing unit to the length of the cylinder may be equal to or about 1:4.

In the continuation of the process, referring now to FIG. 3D, the dosing unit 2 then is rotated about its longitudinal axis to switch from the process of filling the dosing unit 2 to the process of dispensing from the dosing unit 2. In this stage, the dosing unit 2 is rotated until the single opening 2a is in front of the dispensing conduit 5, as shown in FIG. 3E, such that a fluid connection is established between the variable volume 6 of the dosing unit 2 and the dispensing conduit 5 through the single opening 2a.

When the piston 3 is now retracted back into the dosing unit 2, as shown in FIG. 3F, the substance contained in the variable volume 6 is dispensed, for example to an infusion set, through the single opening 2a and the dispensing conduit 5. The piston 3 can be retracted until the dosing unit 2 is completely emptied or, as shown in FIG. 3G, almost completely emptied. Thereby, the piston 3 is maximally retracted into the dosing unit 2 on reaching a front end or a dispensing end of the dosing unit 2.

The dosing unit then can be switched again, as shown in FIG. 3H, to refill the variable volume 6 after a dispensing process has been completed. To switch the dosing device, the dosing unit 2 is rotated again, such that the single opening 2a again lies in front of the supply conduit 4, as shown in FIG. 3A.

In some embodiments, the rotations of the dosing unit 2 shown in FIGS. 3D and 3H, may be made always in the same direction relative to the longitudinal axis of the cylinder, such as, for example, always clockwise or always counterclockwise. Alternatively, it is also possible for the dosing unit 2 to be rotated in a first direction to switch from the filling process to the dispensing process (such as, for example, to the left as shown in FIG. 3D) and to be rotated in the opposite direction to switch from the dispensing process to the filling process (such as, for example, to the right as shown in FIG. 3H). This is particularly advantageous when a back-and-forth movement of the piston 3 is realized using a single motor and the motor is also used to move the dosing unit 2 back and forth or to rotate the dosing unit 2.

FIG. 3I shows a perspective view of an example embodiment of sealing element 7, 8 with the passage (sealing element opening 7a and/or 8a) arranged in it, to which the supply conduit 4 is connected (in the states in accordance with FIGS. 3A to 3C), to which the dispensing conduit 5 is connected (in the states in accordance with FIGS. 3E to 3G), or both.

FIGS. 4A-4H show an embodiment of an operational sequence similar to the embodiment shown in FIG. 3. A dosing unit 2 comprises two supplying/dispensing ports for filling and dispensing, configured as a supply opening 4a and a dispensing opening 5a. The supply opening 4a and the dispensing opening 5a are disposed on one side of the dosing unit 2. The supply opening 4a and the dispensing opening 5a can be arranged in many configurations such as, for example, opposite each other in relation to the center of the dosing unit 2. A sealing element 7, continuously through which a sealing element opening 7a is provided, is disposed in front of the supply opening 4a and the dispensing opening 5a of the dosing unit 2. As shown in the figures, the dosing unit 2 is operable in one of three states. In a first state, depicted in FIGS. 4A, 4B, and 4C, the supply opening 4a is open and the dispensing opening 5a is closed. In a second state, depicted in FIGS. 4D and 4H, both the supply opening 4a and the dispensing opening 5a are closed. In a third state, depicted in FIGS. 4E, 4F, and 4G, the dispensing opening 5a is open and the supply opening 4a is closed. The dosing unit 1 may be rotated, displaced, or both, to select the first state, the second state, or the third state at any given time.

An example embodiment of a sealing element 7 is shown in FIG. 4I. The sealing element 7 can be rotated or moved relative to the dosing unit 2, the supply conduit 4, and the dispensing conduit 5. The dosing unit 2, the supply conduit 4 and the dispensing conduit 5 are preferably in a defined or fixed positional relationship. In the various positions of rotation of the sealing element 7 with the sealing element opening 7a disposed therein, supply opening 4a and dispensing opening 5a may at any given time be both sealed (as in the switching processes shown in FIGS. 4D and 4H), or be alternately opened (as in the filling process of FIGS. 4A-4C and the dispensing process of FIGS. 4E-4G).

During the filling process as shown in the sequence of FIGS. 4A, 4B, and 4C, the sealing element opening 7a of the sealing element 7 is disposed in a position at which a fluid connection can be established between the supply conduit 4 and the variable volume 6. To switch between the filling process and the dispensing process, the sealing element 7 may be rotated about its center axis, as shown in FIG. 4D, until the sealing element opening 7a of the sealing element 7 is arranged as shown in FIG. 4E. Namely, the sealing element opening 7a of the sealing element 7 is arranged so that, for example, the supply opening 4a of the dosing unit 2 is sealed and so that the dispensing opening 5a of the dosing unit is in fluid connection to the dispensing conduit 5. Thereupon, the dispensing process may be performed as shown in the progression from FIG. 4E to FIG. 4F to FIG. 4G.

It is then possible to switch from the dispensing process back to the filling process, as shown in FIG. 4H, wherein the sealing element 7 is rotated so that the sealing element opening 7a of the sealing element 7 is in the position shown in FIG. 4A.

FIG. 4I shows a perspective view of the sealing element 7, comprising a sealing element opening 7a that is offset in the radial direction from the center point of the sealing element 7, where the center axis 11 of the sealing element intersects the surface of the sealing element 7 (depicted as an x).

The invention claimed is:

1. A method for dosing a substance, the method comprising:
providing a dosing device, the dosing device comprising
a dosing unit having a variable volume contained within the dosing unit and at least one opening in fluid connection with the variable volume,
a supply conduit connected to the dosing unit and in fluid connection to a reservoir containing the substance, and
a dispensing conduit connected to the dosing unit and in fluid connection to a dispensing unit of an infusion system,
the dosing unit being operable in a first state in which the variable volume is in fluid connection to the reservoir through the at least one opening but is not in fluid connection to the dispensing conduit, in a second state in which the variable volume is in fluid connection to neither the reservoir nor the dispensing conduit, or in a third state in which the variable volume is in fluid connection to the dispensing conduit through the at least one opening but is not in fluid connection to the reservoir, wherein the dosing unit is operable to be moved to select the first state, the second state, or the third state;
selecting the first state of the dosing unit;
filling the substance into the variable volume through the supply conduit and the single opening, such that the variable volume enlarges while the substance enters the variable volume;
moving the dosing unit so as to move, rotate, or displace the at least one opening and select the third state of the dosing unit; and
dispensing the substance through the at least one opening and into the dispensing conduit by decreasing the volume of the variable volume.

2. The method of claim 1, wherein the dosing unit comprises a piston disposed within a cylinder and wherein, during the dispensing, the volume of the variable volume is decreased by moving the piston.

3. The method of claim 1, wherein the dosing unit is configured so that, during the filling or the dispensing, a predetermined intermediate volume of the variable volume between a minimum volume of the variable volume and a maximum volume of the variable volume can be generated to establish a dose setting, the dose setting defining a volume less than the maximum volume of the variable volume.

4. The method of claim 3, wherein the dosing unit comprises a piston disposed within a cylinder and the dose setting is established by moving the piston to an intermediate position so as to generate the predetermined intermediate volume of the variable volume.

* * * * *

UNITED STATES PATENT AND TRADEMARK OFFICE
CERTIFICATE OF CORRECTION

| | | |
|---|---|---|
| PATENT NO. | : 8,277,434 B2 | Page 1 of 1 |
| APPLICATION NO. | : 13/097894 | |
| DATED | : October 2, 2012 | |
| INVENTOR(S) | : Ulrich Haueter et al. | |

It is certified that error appears in the above-identified patent and that said Letters Patent is hereby corrected as shown below:

Col. 4, Line 7, "enlarge the variable the volume" should read --enlarge the variable volume--

Col. 5, Line 6, "the indicator or controlled" should read --the indicator or controller--

Signed and Sealed this
Twenty-seventh Day of November, 2012

David J. Kappos
*Director of the United States Patent and Trademark Office*